US006764498B2

(12) United States Patent
Mische

(10) Patent No.: US 6,764,498 B2
(45) Date of Patent: Jul. 20, 2004

(54) METHODS AND DEVICES FOR TREATMENT OF NEUROLOGICAL DISORDERS

(76) Inventor: Hans Alois Mische, 32 Highbanks Pl., St. Cloud, MN (US) 56301

( * ) Notice: Subject to any disclaimer, the term of this patent is extended or adjusted under 35 U.S.C. 154(b) by 318 days.

(21) Appl. No.: 10/056,323

(22) Filed: Jan. 24, 2002

(65) Prior Publication Data

US 2002/0065530 A1 May 30, 2002

Related U.S. Application Data

(63) Continuation-in-part of application No. 09/457,971, filed on Dec. 9, 1999, now Pat. No. 6,375,666.

(51) Int. Cl.$^7$ .............................................. A61M 29/00
(52) U.S. Cl. ...................................................... 606/198
(58) Field of Search ................................ 606/191–198, 606/108; 623/1.15, 1.16, 1.22; 600/411, 417, 423

(56) References Cited

U.S. PATENT DOCUMENTS

| 4,312,353 A | * | 1/1982 | Shahbabian | 606/192 |
| 5,342,348 A | * | 8/1994 | Kaplan | 606/198 |
| 6,126,672 A | * | 10/2000 | Berryman et al. | 606/198 |

* cited by examiner

Primary Examiner—Kevin T. Truong

(57) ABSTRACT

A device controls various neurological disorders resulting from improper electrical conduction.

3 Claims, 6 Drawing Sheets

METHODS AND DEVICES FOR TREATMENT OF NEUROLOGICAL DISORDERS

This application is a continuation-in-part of application Ser. No. 09/457,971, filed Dec. 9, 1999, now U.S. Pat. No. 6,875,666.

FIELD OF INVENTION

The present invention relates generally to the treatment of electrical conduction defects in the body. The device and methods are disclosed in the context of treating neurologic disorders.

BACKGROUND OF THE INVENTION

The current methods of treating a range of neurological disorders include the use of systemic drugs, surgical procedures, tissue ablation, and gene treatments. Many of these disorders are manifested by gross conduction defects.

SUMMARY

In contrast to the prior art, the present invention proposes treatment of neurological disorder by subjecting selected tissues to localized mechanical stress. It is difficult to quantify the level of stress applied to the tissue; operable values will vary from low levels to high levels dependent on the type and location of tissue to be treated.

The invention is disclosed in the context of neurologic disorders but other organs and anatomical tissues are contemplated as well.

For example, other applications of this invention include placement in the pituitary, thyroid, and adrenal glands or in a variety of organs. In addition, placement of the inventive device in tumors may suppress growth due to nerve and vascular compression. The later may prevent blood-born metastasis to other parts of the body.

Likewise, hemorrhaging can be stopped or reduced by vascular compression using the invention. Pain management in all parts of the body can be achieved by placement of the inventive device adjacent to selected nerves. Positioning an inventive stress-inducing device within the bone can accelerate healing of broken bones. Disclosure of this invention for neurologic applications is intended to be illustrative and not limiting.

Many neurological disorders are a result of improper conduction of electrical currents in various brain tissues. In the case of Parkinson's disease, the conduction currents in the thalamus tissues become disorganized and cause conditions associated with the disease. Likewise, in epilepsy errant currents cause various levels of seizures. In cases of dystonia, errant currents originate in the basal ganglia. Depression and schizophrenia are associated with various conduction defects in other portions of the brain. Also, pain symptoms such as trigeminal neuralgia are associated with multiple sclerosis. Paralysis is normally a condition that results from brain injury, nerve damage, or nerve severing.

The localized stresses generated by the Mechanical Stress Device (MSD) will control, inhibit and direct current conduction by reorienting and/or reorganizing the electrical bias of them neurological tissues. In addition, applications for the MSD include compression of selected nerves in order to control, mediate, or suppress conduction along the nervetibers and bundles that are associated with certain neurologic disorders.

The MSD can also be utilized as an electrically conductive device that creates an electrical connection or "bridge" between targeted anatomical tissues. This technique may facilitate tissue-to-tissue communication or aid in regenerating nerve connections.

In the case of Parkinson's disease, an MSD is implanted in the tissues proximate to the thalamus and induce localized stresses that cause depolarization of the thalamus tissue and thus eliminate or reduce the symptoms of the disease. In Dystonia, the MSD is positioned proximately to the basal ganglia and disrupts the electrical disturbances associated with this disorder.

The same effect is utilized in the treatment of epilepsy and other tissues when the MSD is installed in the target tissues. The devices and methods associated with the MSD can also be utilized in the sinuses and various ventricles of the brain to treat personality disorders such as schizophrenia or depression. Additionally, migraine headaches may be treated with the MSD technology. In general, the methods of the invention guide the placement of the device to ensure a therapeutic effect from the device.

The MSD can be permanently implanted or used acutely and then removed. Likewise, the device can be fabricated of biodegradable materials that are placed chronically and allowed to biodegrade over time.

The devices and methods can be used alone of in conjunction with other therapies.

Examples of electrical therapy are given and they include pacing, depolarization and ablation.

BRIEF DESCRIPTION OF THE DRAWINGS

Throughout the several views of the drawings several illustrative embodiments of the invention are disclosed. It should be understood that various modifications of the embodiments might be made without departing from the scope of the invention. Throughout the views identical reference numerals depict equivalent structure wherein.

DETAILED DESCRIPTION

The device and methods, which are similar to those discussed in the patent application filed on Nov. 19, 1999 by Mische entitled, "Mechanical Devices for the Treatment of Arrhythmias which is incorporated by reference herein.

Throughout the description the term mechanical stress device MSD refers to a device that alters the electrical conduction of physiologic tissues. The device may be made of metal such as Nitinol or Elgiloy and it may form an electrode for electrical stimulation. One or more electrodes may be associated with it. The MSD may incorporate fiber optics for therapeutic and diagnostic purposes. The device may also be made from a plastic or other non-metallic material. The MSD may also incorporate a covering of polymer or other materials. The MSD may also be a composition of different materials. The MSD may be smooth or have cutting or abrasive surfaces.

The MSD may be implanted for chronic use or for acute use. Biodegradable materials that degrade or dissolve over time may be used to form the MSD. Various coatings may be applied to the MSD including, but not limited to, thrombo-resistant materials, electrically conductive, non-conductive, thermo-luminescent, heparin, radioactive, or biocompatible coatings. Drugs, chemicals, and biologics such as morphine, dopamine, aspirin, lithium, Prozac, genetic materials, and growth factors can be applied to the MSD in order to facilitate treatment.

Other types of additives can be applied as required for specific treatments. Electrically conductive MSDs or MSDs with electrode elements may be used with companion pulse generators to deliver stimulation energy to the tissues. This electrical therapy may be used alone or in combination with other therapies to treat the various disorders. Electrical therapies may be supplied from implantable devices or they may be coupled directly to external generators. Coupling between the MSD and external generators can be achieved using technologies such as inductive or microwave coupling as examples. The MSD may also be designed of geometries or materials that absorb radioactive energies.

Figure 1:
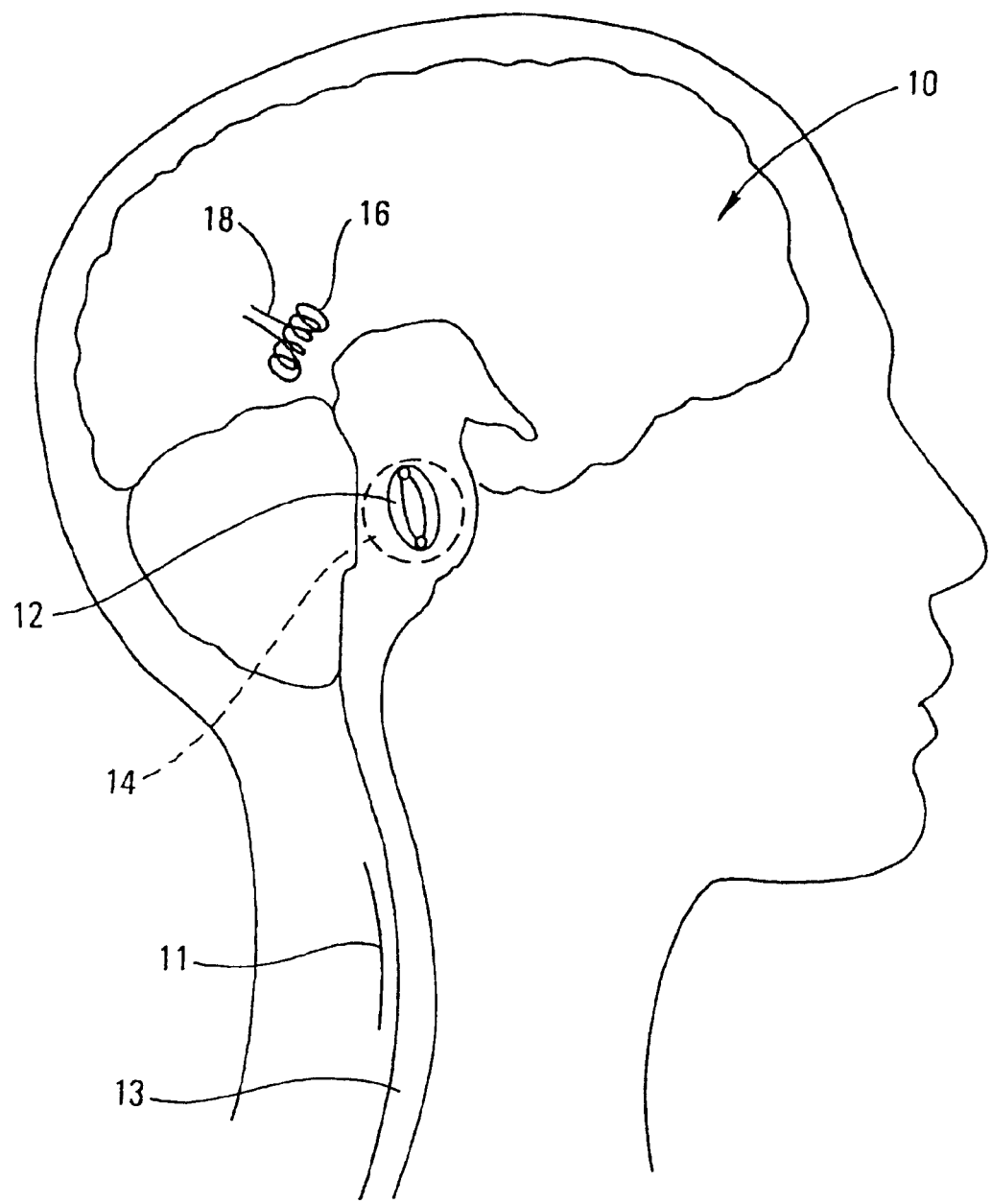
FIG. 1. is a schematic diagram of the head showing mechanical stress devices implanted within brain tissue.

FIG. 1 is a schematic diagram showing several possible locations and geometries for the mechanical stress device (MSD) within the brain 10. A multi-element splined MSD 12 is positioned proximate to the thalamus 14. In this case, the treatment is for Parkinson's Disease. A coil MSD 16 is positioned proximate to the trigeminal nerve 18 for treatment of trigeminal neuralgia. A wire form MSD 11 is positioned adjacent to the spinal cord 13.

Figure 2:
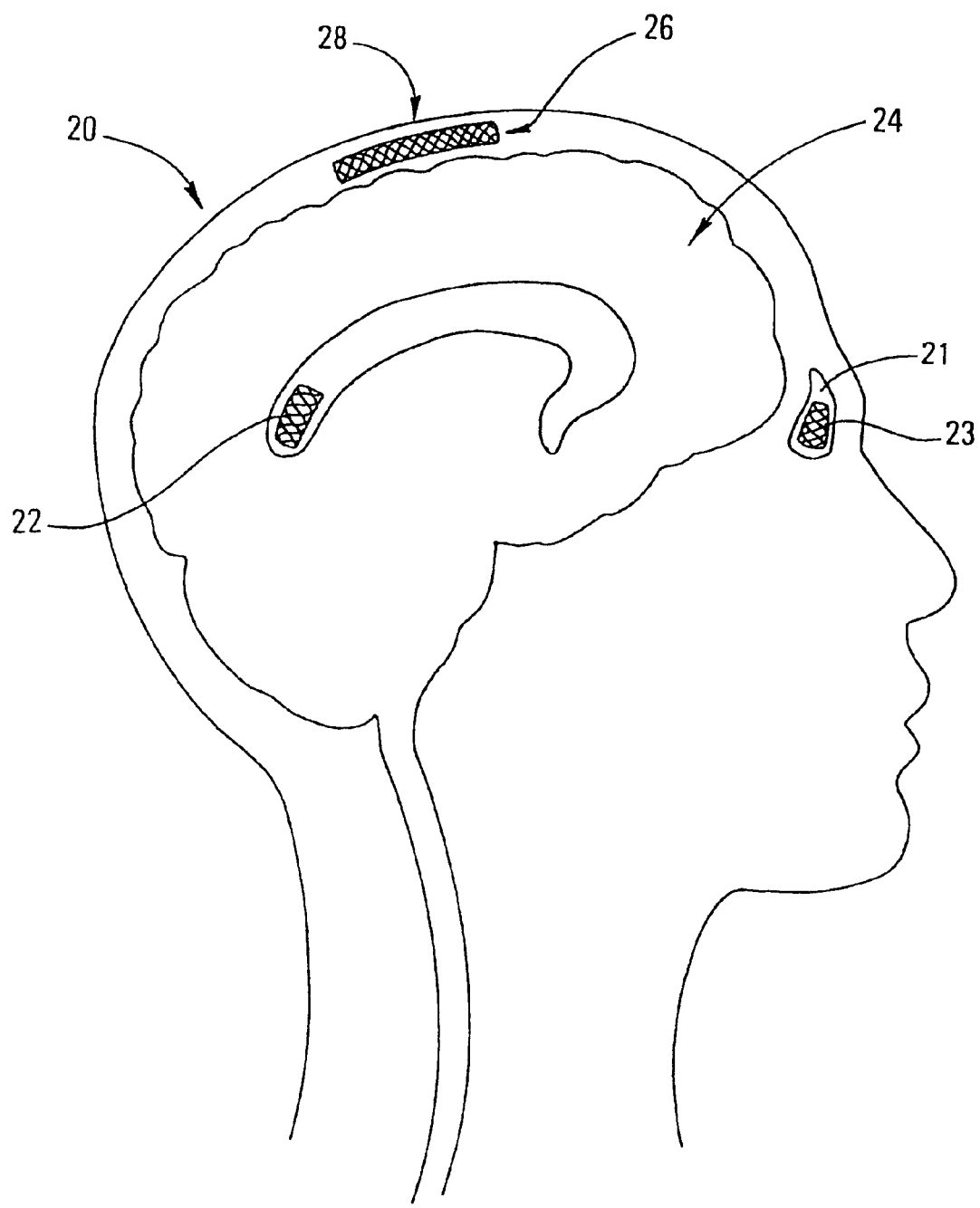
FIG. 2. is a schematic diagram of the head showing mechanical stress devices implanted in the frontal sinus, lateral ventricle of brain, and between the skull and brain tissue.

FIG. 2. is a schematic diagram of the head showing 20 various locations of MSDs of a tubular mesh form. An MSD 22 is located in the lateral ventricle of the brain 24. Another MSD 26 is positioned between the skull 28 and the brain 24. Within the frontal sinus 21 an MSD 23 is positioned.

Figure 3:
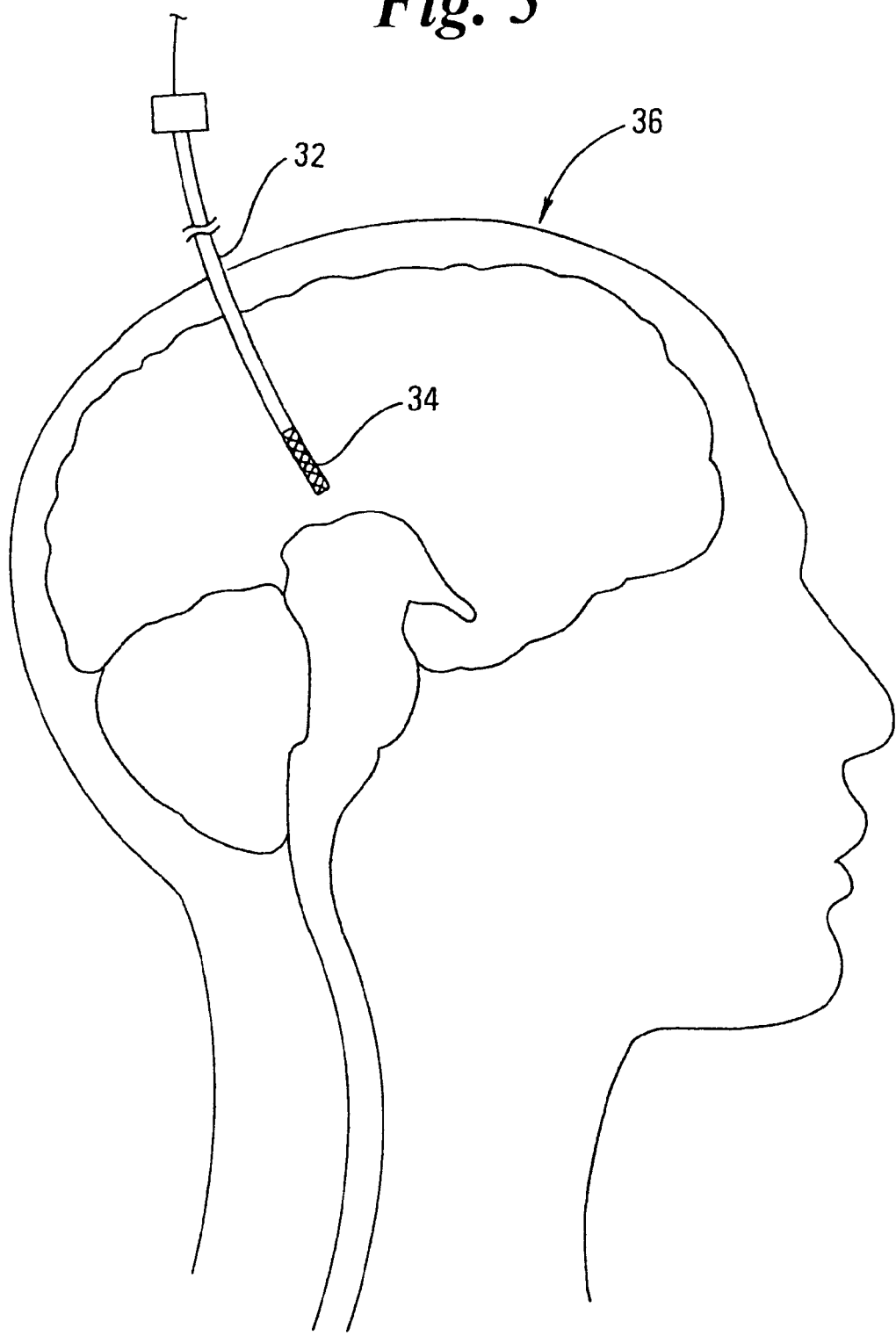
FIG. 3. is a schematic diagram of the head showing the mechanical stress device delivery system.
Figure 4:
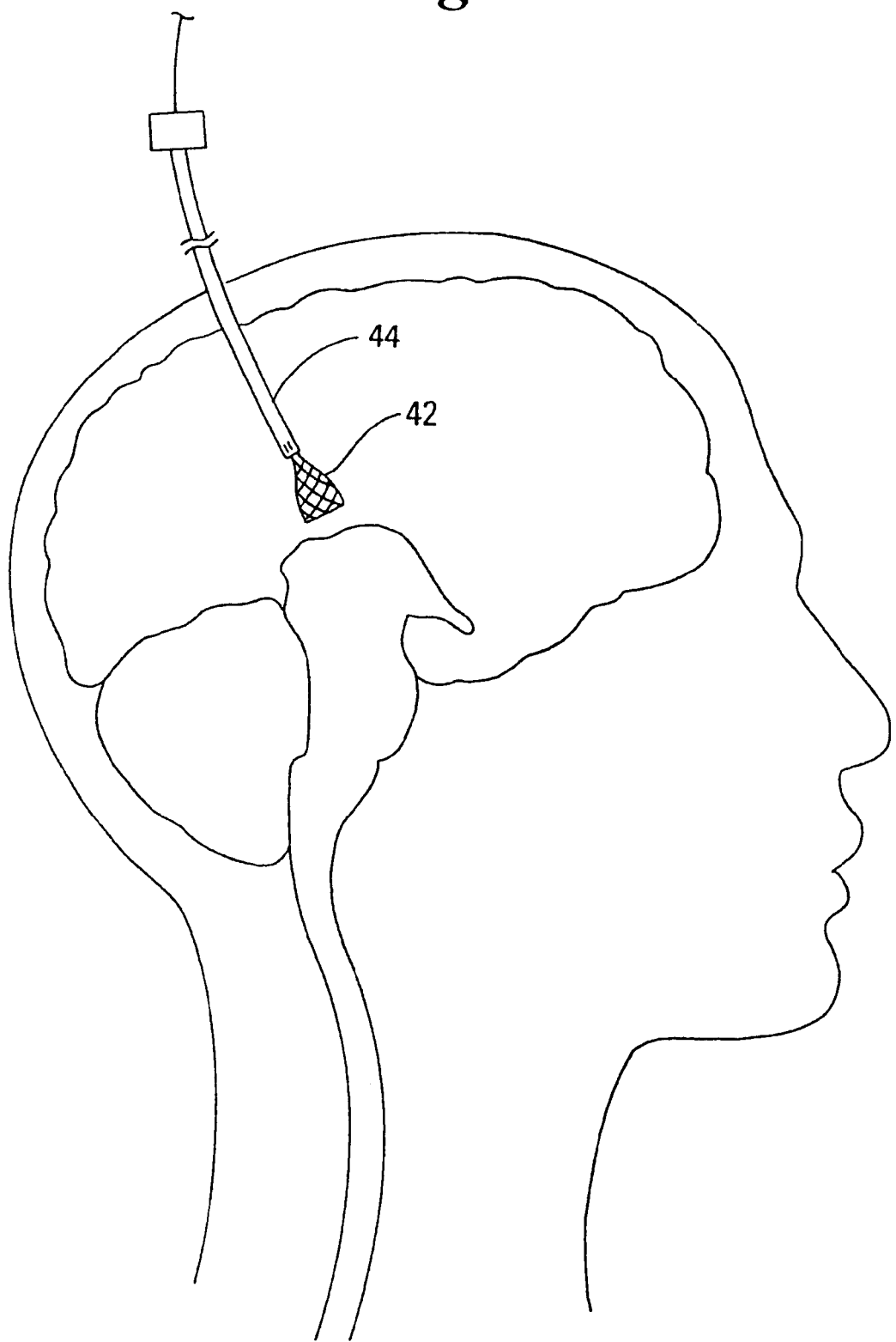
FIG. 4. is a schematic diagram of the head showing the mechanical stress device delivery system.

FIG. 3 and FIG. 4 should be considered together. Together the two figure show the deployment of an MSD.

FIG. 3 is a schematic diagram of a tubular mesh type MSD delivery system. The tubular catheter 32 delivers the tubular mesh MSD 34. The first stage of implantation is navigation of the device to the selected site through the skull 36.

FIG. 4 shows the tubular mesh 42 expanding into position as it emerges from the lumen of the delivery catheter 44. In the self-expanding case, the tubular mesh has a predetermined maximum expandable diameter. The mesh can be made of a shape-memory material such as Nitinol so that when subjected to body temperature the structure expands. With shape memory materials, the shape of the expanded device can be predetermined. Additionally, the device can be retrieved, repositioned, or removed by using its shape memory characteristics. In general the MSD may be used acutely or chronically depending on the disease state of the patient.

Figure 5:
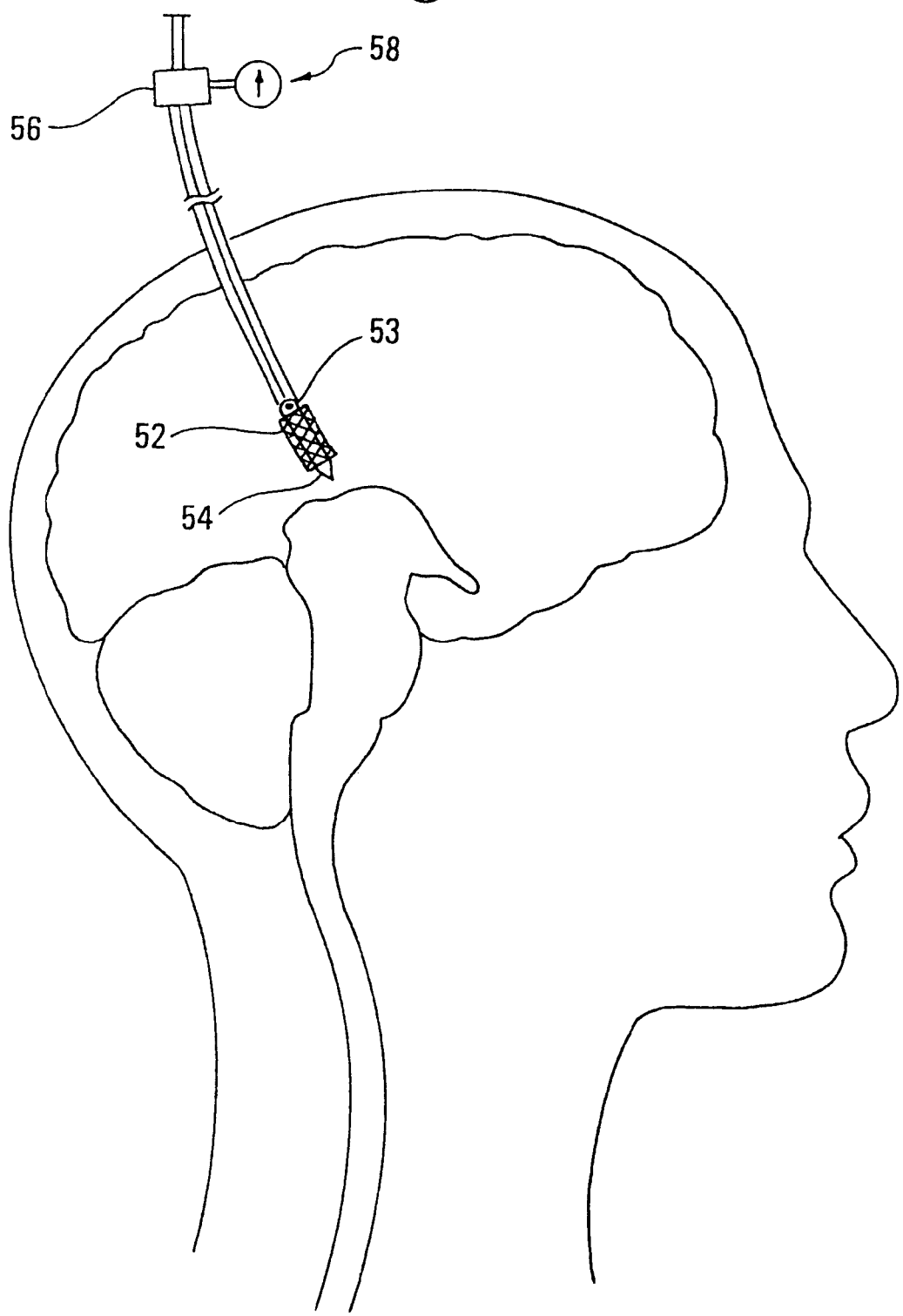
FIG. 5. is a schematic diagram of the head showing the mechanical stress device delivery system.

FIG. 5 shows an alternate balloon expanded MSD 52. In this alternate embodiment a balloon 54 may be used to expand the device within or proximate to selected tissues. In the balloon expandable case, the balloon may have a predetermined minimum or maximum diameter. In addition, the balloon shape can be made to provide proper placement and conformance of the device based on anatomical requirements and location. The balloon may be covered with electrically conductive material. The balloon may be inflated via a syringe 56 and a pressure gauge 58. For example an electrode site 53 may be connected to a remote pulse generator (not shown) to stimulate or ablate the site. The stimulator may activate the electrode either chronically or acutely.

Figure 6:
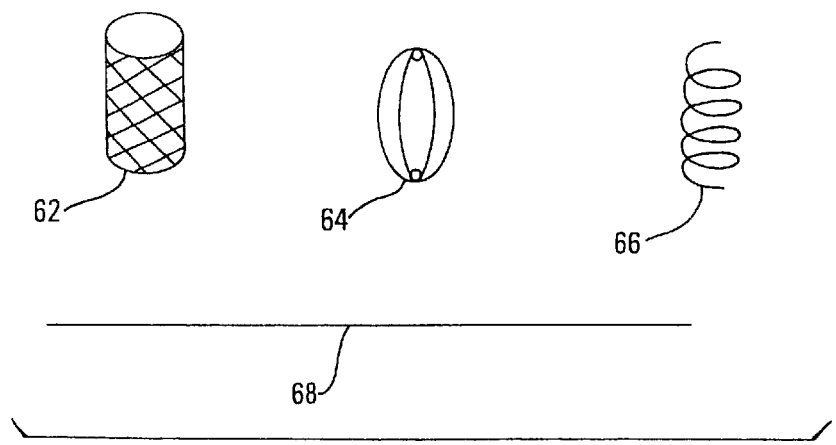
FIG. 6. shows a variety of MSD designs.

FIG. 6 shows a variety of possible MSD shapes and geometries. A tubular mesh 62, a multi-element spline 64, a coil 66, a wire 68 are all acceptable shapes for the MSD although each shape may be specifically adapted to a particular disease state.

Figure 7:
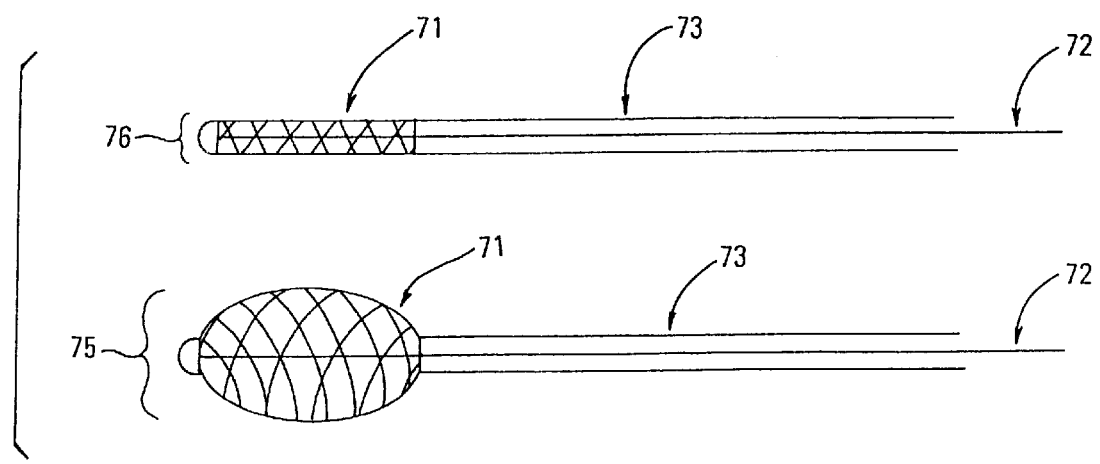
FIG. 7. depicts an MSD, which is man d contracted.

FIG. 7 shows two states of a manually expandable MSD device 71. The device consists of a coaxial shaft 72 and tube 73 arrangement. Attached to the distal end of the shaft 72 and the tube 73 is a braided mesh tube MSD 71. When the shaft 72 and tube 73 are moved opposite of the other by manipulating the proximal ends, the MSD 71 expands 75 or contracts 76. In this case, the MSD 71 can be made of any structure that expands and contracts such as a coil, splined-elements, etc. The various methods of expanding and contracting these structures are, but not limited to, push-pull, rotation, and balloon manipulation. In this type of device, direct connection to either an electrical generator, laser, or monitoring system can be made. In addition, it be envisioned that a device of similar nature be connected to a mechanical energy source, such as rotational or vibrational, in order to increase localized stresses.

The MSD can also utilize devices such as a balloon catheter, expanding devices, or wedges that impart stress or certain levels of localized trauma to selected tissues. The resultant stress and trauma affect the tissues so that current conduction in modified. It is envisioned that any of these devices can be used alone or in conjunction with other treatment modalities in order to provide the desired therapeutic result.

In general, the MSD will have a relaxed or minimum energy state. However the device or the implantation procedure should stretch or stress the device so that it applies a persistent force to the tissues to alter conduction in the strained tissues. In this sense the implanted MSD is not in a fully relaxed state after implantation. In some instances the MSD will cause the tissues to yield or tear generating altered conduction.

Preferably, the MSD is delivered in a minimally invasive procedure such via a catheter or other device. X-ray imaging, fluoroscopy, MRI, CAT scan or other visualization means can be incorporated into the procedural method. In general the devices may be introduced with cannulas, catheters or over guidewires through naturally occurring body lumens or surgically prepared entry sites. It should be apparent that other surgical and non-surgical techniques can be used to place the devices in the target tissue.

It should be apparent that various modifications might be made to the devices and methods by one of ordinary skill in the art, without departing from the scope or spirit of the invention.

In another embodiment, MSD's may also be designed in order to optimize coupling with external sources of electromagnetic energies via inductive or capacitive coupling. These energies can be utilized to electrically activate the MSD in order to impart voltages and currents to tissues to augment the mechanoelectric effects of the MSD. The MSD can be designed in such a fashion where it acts similarly to an implanted antenna. Likewise, the MSD may function primarily as an antenna with little, if any, mechanoelectric effects. The coupled electrical energy to this MSD antenna can be directly imparted to the tissues adjacent to the implanted. The received energy may be used to charge a circuit that is integrated into the MSD structure that discharges at a certain level, directing electrical energy to the desired or adjacent tissue. For example, the circuit may consist of resistors, capacitors, inductors, amplifiers, diodes or other components that assist in producing the desired function and effects. The circuit may consist of separate nodes for input and output voltages or it may have one node for both input and output.

In another embodiment, the MSD may consist of circuitry that can automatically treat the neurologic defects by utilizing the electrical energy generated by the physiologic tissues in which the MSD is implanted. In the case of epilepsy, focal tissues generate errant currents that result in seizure activity. These affected focal tissues are readily identified with standard CAT or MRI imaging systems and an MSD can then be implanted into these tissues. When the errant currents are generated, these currents charge the circuitry in the MSD. When the circuitry is charged to a predetermined level, it discharges back into the affected focal tissues and resolves the errant currents. A RC time constant circuit can be utilized for this MSD version. Amplifiers, signal generators and other processing circuitry can be incorporated into an MSD in order to increase or modify the output.

In another embodiment, the MSD has a covering to increase the surface area of the device. The covering can be encompass the entire device or selected portions and can be positioned on the outside or inside surface. Such a covering can be made of polymers such as Teflon, polyethylene, polyurethane, nylon, biodegradable materials or other polymeric materials. The covering can also be made of a fine metal or polymeric mesh. In all cases, the covering can be bonded to the surface of the MSD or applied as a loose sheath-type covering. The covering can have therapeutic materials applied or incorporated into the covering material itself. Examples of the therapeutic materials include drugs, stem cells, heparin, biologic materials, biodegradable compounds, collagen, electrolytes, radiopaque compounds, radioactive compounds, radiation-activated substances, or other materials that enhance the clinical effects and/or procedures.

In another embodiment, the MSD may have a material that substantially fills its interior space. Such a material would prevent formation of spaces or voids once an expandable MSD is placed. The materials may be fibrous, gels, porous, foam or sponge-like and may be incorporated with polymers, glass, metals, radioactive compounds, biologic tissues, drugs, or other suitable materials that may enhance clinical effective and/or procedures. The materials would be flexible enough to allow expansion of the MSD and can be made of polymers, glass, metal, biologic tissues, drugs, or other suitable materials. Although not limited to, examples of biologic materials include stem cells, brain cells and matter, thalamic tissues, and collagen.

The use of appropriate materials may also provide certain electrical properties to the MSD that enable it to receive, store and/or transmit electrical energy. The dielectric properties of these materials would provide electrical capacitor properties and function to the MSD. This provides the benefit of creating an electrical circuit that can receive, store and discharge energy from various sources. The source may be external generators that couple, capacitively or inductively, RF energy from a predetermined portion of the electromagnetic spectrum to the MSD. In addition, the source may be an electrical generator connected by a wire or a cable to the MSD.

Another means of generating therapeutic electrical energy is to utilize galvanic effects. Proper material selection and interaction with physiologic fluids and tissues would result in galvanic currents or electrochemical reactions being generated by the MSD. Generally, dissimilar metals or materials would be used in order to optimize the generation of galvanic currents. These currents could provide constant therapeutic electrical energy levels to the desired tissues. This could potentially benefit patients suffering from Parkinson's, epilepsy, pain, depression, migraines, etc. The galvanic a currents can also be used to energize, activate, or charge circuits or batteries that provide monitoring, diagnostic or therapeutic effects. This technology could also be used for intravascular devices such as stents in order to prevent thrombosis or hyperplasia or to energize implantable sensors or monitoring devices. Galvanic devices can also be used to treat peripheral pain, generate revascularization of myocardial tissues, treat tumors, provide electrical potential for drug transport into tissues, treat endometriosis, or to power, energize, activate, operate or charge other medical devices such as cardiac pacemakers, defibrillators or other electrical generator based systems.

In another embodiment, the MSD may be a structure that completely or partially slices into tissue. The slicing action cleaves or separates the tissue physically breaking the electrical conduction paths. In this case, the MSD can reach complete or partial state of expansion. In the case of complete expansion, the residual stress to the tissue would be approaching zero, while the partial expansion would result in a combined clinical effect via part mechanical stress and part slicing of tissue.

Additional methods of constructing MSD's include using three-dimensional structures such as wedges, slugs, clips, rivets, balls, screws, and other structures that impart stress to the tissues. Materials such as open-cell polymers, gels, liquids, adhesives, foams can also be inserted or injected into tissue and tissue spaces in order to generate the desired amount of stress. These types of material could also have the additional benefit of being therapeutic agents or carriers for therapeutic agents.

Another MSD structure can consist of a balloon that is positioned at desired location, inflated within the tissue, and then detached and left in an inflated state. Examples of inflation media can be fluids, gels, foams, pharmaceuticals, and curable resins.

Other embodiments of MSD composition include construction using magnet and magnetic materials that complement the localized effects of the MSD by controlling the electrical properties of the tissues using gradients and fields. In the case where the MSD is composed of magnet materials, the magnetic field emanating from the magnetic materials would bias electric fields within the tissues. This effect can control the direction of current conduction within the tissues. In the case where the MSD is composed of magnetic materials that interact with magnetic gradients and fields, an external magnet placed proximate to the head can physically manipulate the MSD. Movement of the magnetic would cause movement of the MSD. The manipulation would result in dynamic stresses to the tissues adjacent to the MSD, thus affecting the electrical properties of the tissues and potentially resolving seizures or tremors.

Other MSD can be built with an integrated circuit consisting of a resistor, capacitor, and an inductor. The inductor couples with the external electromagnetic energy and the resulting current generated in the inductor charges the capacitor. Based on the RC time constant of the circuit, the capacitor charges to a certain level and then discharges directly to the desired tissues and the errant currents are disrupted by this discharge. A combination of electromagnetic coupling and direct connection incorporates a generator with a transmission coil and a ground connection made directly to the patient, providing a closed-loop circuit. The ground connection can be made directly to the skin of the patient using a clip or a grounding pad such as used during electrosurgical procedures. The pad may be applied to the patient with tape, bands or adhesives. The ground connection may also be implanted on or within tissue. External generators may be manually operated by the patient or other person or may be automatically operated utilizing monitoring systems that identify seizures or tremors and energize the MSD. Likewise, automatic circuitry such as the aforementioned RC-timing circuit can be used. The generators may also be programmed to energize at a certain predetermined sequence, rate and level. In the treatment of mania, depression, schizophrenia or similar disorders, the generator may provide a constant output to maintain a consistent state of electrical condition of the tissues. For convenience, the external generators may be attached directly to the head or incorporated into a hat, helmet, or band. Alternately, the transmission coil separately may be attached directly to the head or incorporated into a hat, helmet, scarf or band. The coil may encompass the entire head or specific portions in order to attain desired coupling with the MSD.

Likewise, as mentioned previously, the electrical energy inherent in physiologic tissue may also be the source that energizes the circuit. Again, it should be noted that various modifications might be made to the devices and methods by one of ordinary skill in the art, without departing from the scope of the invention.

What is claimed:

1. A method of treating neurologic disorder involving electrical an conduction defects comprising the steps of:

identifying target tissue having the electrical conduction defect responsible for the neurologic disorder;

placing a mechanical stress device in said target tissue with a placement device;

removing said placement device, whereby said mechanical stress device remains in said tissue;

whereby said mechanical stress device is activated by the inherent physiologic currents to treat said neurological disorder.

2. A method of treating neurologic disorder involving electrical an conduction defects comprising the steps of:

identifying target tissue having the electrical conduction defect responsible for the neurologic disorder;

placing a mechanical stress device in said target tissue with a placement device;

removing said placement device, whereby said mechanical stress device remains in said tissue;

whereby electrochemical processes generate currents in said mechanical stress device to affect electrical conduction of said tissue to treat said neurological disorder.

3. A method of treating neurologic disorder involving electrical an conduction defects comprising the steps of:

identifying target tissue having the electrical conduction defect responsible for the neurologic disorder;

placing a mechanical stress device in said target tissue with a placement device;

removing said placement device, whereby said mechanical stress device remains in said tissue;

activating an externally positioned electromagnetic generator; whereby said generator electromagnetically activates said mechanical stress device to affect electrical conduction of said tissue to treat said neurological disorder.

* * * * *